US012369804B2

(12) United States Patent
He

(10) Patent No.: US 12,369,804 B2
(45) Date of Patent: *Jul. 29, 2025

(54) SENSING PHYSIOLOGICAL PARAMETERS THROUGH AN ARTICLE

(71) Applicant: Verily Life Sciences LLC, South San Francisco, CA (US)

(72) Inventor: David He, South San Francisco, CA (US)

(73) Assignee: Verily Life Sciences LLC, Dallas, TX (US)

( * ) Notice: Subject to any disclaimer, the term of this patent is extended or adjusted under 35 U.S.C. 154(b) by 204 days.

This patent is subject to a terminal disclaimer.

(21) Appl. No.: 18/162,953

(22) Filed: Feb. 1, 2023

(65) Prior Publication Data
US 2023/0210391 A1    Jul. 6, 2023

Related U.S. Application Data

(63) Continuation of application No. 16/841,129, filed on Apr. 6, 2020, now Pat. No. 11,607,143.
(Continued)

(51) Int. Cl.
*A61B 5/024* (2006.01)
*A61B 5/00* (2006.01)
(Continued)

(52) U.S. Cl.
CPC ........ *A61B 5/02427* (2013.01); *A61B 5/0059* (2013.01); *A61B 5/0205* (2013.01);
(Continued)

(58) Field of Classification Search
CPC ............ A61B 5/02427; A61B 5/02416; A61B 5/0059; A61B 5/0205; A61B 5/6808
See application file for complete search history.

(56) References Cited

U.S. PATENT DOCUMENTS 3,013,257 A    12/1961 Ippolito
3,261,987 A    7/1966 Chapin
(Continued)

FOREIGN PATENT DOCUMENTS

CN    1607928 A    4/2005
CN    104605992 A    5/2015
(Continued)

OTHER PUBLICATIONS

U.S. Appl. No. 15/292,389, "Corrected Notice of Allowability", Jun. 30, 2020, 2 pages.
(Continued)

*Primary Examiner* — John R Downey
(74) *Attorney, Agent, or Firm* — Kilpatrick Townsend & Stockton LLP

(57) ABSTRACT

Various examples are described for detecting heart rate and respiratory rate by using measurements of light applied to skin through an article. For example, a sensor application obtains a set of measurements of light. The application compensates for a contribution of the article based on one or more known optical properties of the article. The sensor application further determines, from the set of measurements of light, a periodic change in amplitude. The sensor application identifies the periodic change in amplitude as a heart rate having an identical periodicity. The sensor application identifies a respiratory rate as equal to the rate of change of the heart rate.

20 Claims, 8 Drawing Sheets

Related U.S. Application Data

(60) Provisional application No. 62/833,362, filed on Apr. 12, 2019.

(51) Int. Cl.
  *A61B 5/0205* (2006.01)
  *A61B 5/08* (2006.01)
  *A61F 13/42* (2006.01)
  *A61F 13/49* (2006.01)

(52) U.S. Cl.
  CPC ........ *A61B 5/02405* (2013.01); *A61B 5/4809* (2013.01); *A61B 5/6808* (2013.01); *A61B 5/721* (2013.01); *A61F 13/42* (2013.01); *A61F 13/49007* (2013.01); *A61B 5/0816* (2013.01); *A61B 2503/04* (2013.01); *A61B 2562/0219* (2013.01); *A61B 2562/0238* (2013.01); *A61F 2013/422* (2013.01)

(56) References Cited

U.S. PATENT DOCUMENTS

| | | | |
|---|---|---|---|
| 4,128,760 A | 12/1978 | Del Signore, II | |
| 4,315,159 A | 2/1982 | Niwa et al. | |
| 5,069,214 A | 12/1991 | Samaras et al. | |
| 5,079,541 A | 1/1992 | Moody | |
| 5,616,140 A | 4/1997 | Prescott | |
| 5,654,803 A | 8/1997 | Howard, III et al. | |
| 6,147,592 A | 11/2000 | Ulrich et al. | |
| 6,287,253 B1 | 9/2001 | Ortega et al. | |
| 8,111,165 B2 | 2/2012 | Ortega et al. | |
| 8,416,088 B2 | 4/2013 | Ortega et al. | |
| 8,628,506 B2 | 1/2014 | Ales, III et al. | |
| 8,920,332 B2 | 12/2014 | Hong et al. | |
| 8,935,006 B2 | 1/2015 | Vu et al. | |
| 10,117,598 B1 | 11/2018 | Mouradian | |
| 10,568,525 B1* | 2/2020 | Wu ................ A61B 5/6824 |
| 10,575,390 B2 | 2/2020 | Schiffer et al. | |
| 10,722,405 B2 | 7/2020 | Pepin et al. | |
| 10,880,972 B2 | 12/2020 | Schiffer et al. | |
| 11,275,023 B2 | 3/2022 | Schiffer et al. | |
| 11,373,102 B2 | 6/2022 | Pathak et al. | |
| 11,607,143 B2 | 3/2023 | He | |
| 11,679,036 B2 | 6/2023 | Schiffer et al. | |
| 2002/0026164 A1 | 2/2002 | Camarero Roy et al. | |
| 2002/0124295 A1 | 9/2002 | Fenwick et al. | |
| 2004/0022053 A1 | 2/2004 | Sharon et al. | |
| 2005/0019508 A1 | 1/2005 | Engel et al. | |
| 2005/0195085 A1 | 9/2005 | Cretu-Petra | |
| 2006/0244614 A1 | 11/2006 | Long | |
| 2007/0130893 A1 | 6/2007 | Davies | |
| 2007/0142796 A1 | 6/2007 | Mosbacher et al. | |
| 2007/0142799 A1 | 6/2007 | Ales et al. | |
| 2008/0021429 A1 | 1/2008 | Klofta et al. | |
| 2008/0255528 A1 | 10/2008 | Springer et al. | |
| 2008/0262381 A1 | 10/2008 | Kolen | |
| 2008/0300470 A1 | 12/2008 | Gerber et al. | |
| 2009/0157025 A1 | 6/2009 | Song et al. | |
| 2009/0240155 A1 | 9/2009 | Nakayama et al. | |
| 2009/0275908 A1 | 11/2009 | Song | |
| 2010/0164733 A1 | 7/2010 | Ales et al. | |
| 2010/0185068 A1 | 7/2010 | Park et al. | |
| 2010/0241094 A1 | 9/2010 | Sherron | |
| 2010/0290948 A1 | 11/2010 | Song | |
| 2012/0109087 A1 | 5/2012 | Abraham et al. | |
| 2012/0116337 A1 | 5/2012 | Ales et al. | |
| 2012/0302926 A1 | 11/2012 | Tanaka et al. | |
| 2012/0310192 A1 | 12/2012 | Suzuki et al. | |
| 2013/0001422 A1 | 1/2013 | Lavon et al. | |
| 2013/0066289 A1 | 3/2013 | Song et al. | |
| 2014/0121473 A1 | 5/2014 | Banet et al. | |
| 2014/0143183 A1 | 5/2014 | Sigal et al. | |
| 2014/0200538 A1 | 7/2014 | Euliano et al. | |
| 2014/0228712 A1 | 8/2014 | Elliott et al. | |
| 2014/0275854 A1 | 9/2014 | Venkatraman et al. | |
| 2015/0061863 A1 | 3/2015 | Barfield, Jr. et al. | |
| 2015/0105608 A1 | 4/2015 | Lipoma et al. | |
| 2015/0112202 A1 | 4/2015 | Abir | |
| 2015/0150732 A1 | 6/2015 | Abir | |
| 2015/0164377 A1 | 6/2015 | Nathan et al. | |
| 2015/0223755 A1 | 8/2015 | Abir | |
| 2015/0272482 A1 | 10/2015 | Houmanfar et al. | |
| 2015/0288877 A1 | 10/2015 | Glazer | |
| 2015/0297125 A1 | 10/2015 | Montgomery et al. | |
| 2016/0003615 A1 | 1/2016 | Biswas et al. | |
| 2016/0120455 A1 | 5/2016 | Pop et al. | |
| 2016/0256086 A1 | 9/2016 | Byrd et al. | |
| 2016/0287074 A1 | 10/2016 | Pradeep et al. | |
| 2016/0287076 A1 | 10/2016 | Pradeep et al. | |
| 2016/0292576 A1 | 10/2016 | Pradeep et al. | |
| 2016/0292584 A1 | 10/2016 | Weinberg et al. | |
| 2016/0292986 A1 | 10/2016 | Pradeep et al. | |
| 2016/0296144 A1 | 10/2016 | Gaddam et al. | |
| 2016/0310027 A1* | 10/2016 | Han ................... A61B 5/02427 |
| 2017/0049336 A1 | 2/2017 | Hatch | |
| 2017/0128274 A1 | 5/2017 | Varga et al. | |
| 2017/0172433 A1 | 6/2017 | Olivier | |
| 2017/0215808 A1 | 8/2017 | Shimol et al. | |
| 2017/0252225 A1 | 9/2017 | Arizti et al. | |
| 2017/0296397 A1 | 10/2017 | Kunze et al. | |
| 2017/0348162 A1 | 12/2017 | Arizti et al. | |
| 2017/0354547 A1 | 12/2017 | Abir | |
| 2018/0008478 A1 | 1/2018 | Xu | |
| 2018/0056128 A1 | 3/2018 | Narasimha Rao et al. | |
| 2018/0104114 A1 | 4/2018 | Pepin et al. | |
| 2018/0253957 A1 | 9/2018 | Jhangiani et al. | |
| 2018/0333306 A1 | 11/2018 | Ahong et al. | |
| 2018/0353134 A1 | 12/2018 | Walter et al. | |
| 2019/0015000 A1* | 1/2019 | Han ................... A61B 5/681 |
| 2019/0132948 A1 | 5/2019 | Longinotti-Buitoni et al. | |
| 2019/0304000 A1 | 10/2019 | Simpson | |
| 2019/0340515 A1 | 11/2019 | Pathak et al. | |
| 2019/0342973 A1 | 11/2019 | Schiffer et al. | |
| 2020/0022637 A1 | 1/2020 | Kurzrock et al. | |
| 2020/0129380 A1 | 4/2020 | Sazonov et al. | |
| 2020/0163602 A1 | 5/2020 | Pareddy et al. | |
| 2020/0260998 A1 | 8/2020 | Auerbach et al. | |
| 2020/0323450 A1 | 10/2020 | He | |
| 2020/0323700 A1 | 10/2020 | Schiffer et al. | |
| 2021/0068235 A1 | 3/2021 | Schiffer et al. | |
| 2021/0100694 A1 | 4/2021 | Baek et al. | |

FOREIGN PATENT DOCUMENTS

| | | |
|---|---|---|
| CN | 105496356 A | 4/2016 |
| CN | 205246547 U | 5/2016 |
| CN | 105636511 A | 6/2016 |
| CN | 106198538 A | 12/2016 |
| CN | 106464844 A | 2/2017 |
| CN | 107784647 A | 3/2018 |
| CN | 110432908 A | 11/2019 |
| CN | 110441298 A | 11/2019 |
| CN | 210834672 U | 6/2020 |
| EP | 2425771 A2 | 3/2012 |
| EP | 2832323 A1 | 2/2015 |
| JP | 61296239 A | 12/1986 |
| JP | 2002515975 A | 5/2002 |
| KR | 1020090041260 A | 4/2009 |
| WO | 9708523 A1 | 3/1997 |
| WO | 0100117 A2 | 1/2001 |
| WO | 02063260 A2 | 8/2002 |
| WO | 2007128038 A1 | 11/2007 |
| WO | 2012059832 A2 | 5/2012 |
| WO | 2018071365 A1 | 4/2018 |
| WO | 2019213586 A1 | 11/2019 |
| WO | 2019213590 A9 | 12/2019 |

OTHER PUBLICATIONS

U.S. Appl. No. 15/292,389, Final Office Action, Mailed on Dec. 5, 2019, 18 pages.

U.S. Appl. No. 15/292,389, Non-Final Office Action, Mailed on Mar. 7, 2019, 12 pages.

(56) References Cited

OTHER PUBLICATIONS

U.S. Appl. No. 15/292,389, Notice of Allowance, Mailed on Feb. 18, 2020, 8 pages.
U.S. Appl. No. 15/971,306, "Corrected Notice of Allowability", Jan. 31, 2020, 3 pages.
U.S. Appl. No. 15/971,306, Final Office Action, Mailed on Aug. 8, 2019, 8 pages.
U.S. Appl. No. 15/971,306, Non-Final Office Action, Mailed on Jan. 28, 2019, 12 pages.
U.S. Appl. No. 15/971,306, Notice of Allowance, Mailed on Oct. 22, 2019, 9 pages.
U.S. Appl. No. 16/383,136, "Corrected Notice of Allowability", Apr. 4, 2022, 2 pages.
U.S. Appl. No. 16/383,136, Non-Final Office Action, Mailed on Oct. 8, 2021, 39 pages.
U.S. Appl. No. 16/383,136, Notice of Allowance, Mailed on Feb. 24, 2022, 9 pages.
U.S. Appl. No. 16/383,337, Non-Final Office Action, Mailed on Aug. 3, 2022, 26 pages.
U.S. Appl. No. 16/745,771, "Corrected Notice of Allowability", Sep. 14, 2020, 2 pages.
U.S. Appl. No. 16/745,771, "Ex Parte Quayle Action", Jun. 29, 2020, 6 pages.
U.S. Appl. No. 16/745,771, Notice of Allowance, Mailed on Aug. 24, 2020, 9 pages.
U.S. Appl. No. 16/841,129, Non-Final Office Action, Mailed on Feb. 17, 2022, 17 pages.
U.S. Appl. No. 16/841,129, Non-Final Office Action, Mailed on Jul. 14, 2022, 20 pages.
U.S. Appl. No. 16/841,129, Notice of Allowance, Mailed on Nov. 14, 2022, 12 pages.
U.S. Appl. No. 16/949,759, "Corrected Notice of Allowability", Jan. 10, 2022, 2 pages.
U.S. Appl. No. 16/949,759, "Corrected Notice of Allowability", Feb. 7, 2022, 3 pages.
U.S. Appl. No. 16/949,759, Notice of Allowance, Mailed on Nov. 24, 2021, 11 pages.
Application No. CN201920639694.1, Notice of Decision to Grant, Mailed on Jul. 27, 2020, 2 pages.
Application No. CN201920639694.1, Office Action, Mailed on Mar. 27, 2020, 3 pages.
Application No. CN201920640368.2, Notice of Decision to Grant, Mailed on Apr. 20, 2020, 2 pages.
Application No. EP19724681.2, Office Action, Mailed on Jun. 9, 2022, 4 pages.
Application No. EP20787437.1, Extended European Search Report, Mailed on Nov. 30, 2022, 10 pages.
Kastle et al., "A New Family of Sensors for Pulse Oximetry", Hewlett Packard Journal, vol. 48, Feb. 1997, pp. 1-17.
Kim et al., "Miniaturized Battery-Free Wireless Systems for Wearable Pulse Oximetryy", Advanced Functional Materials, vol. 27 No. 1, Jan. 5, 2017, pp. 1-18.
Lara et al., "A Survey on Human Activity Recognition using Wearable Sensors", IEEE Communications Surveys & Tutorials, vol. 15, Issue 3, Nov. 29, 2012, pp. 1192-1209.
Leonard et al., "Standard Pulse Oximeters Can be Used to Monitor Respiratory Rate", Emergency Medicine Journal, vol. 20, No. 6, Nov. 2003, pp. 524-525.
Application No. PCT/US2017/055840, International Preliminary Report on Patentability, Mailed on Apr. 25, 2019, 8 pages.
Application No. PCT/US2017/055840, International Search Report and Written Opinion, Mailed on Nov. 27, 2017, 14 pages.
Application No. PCT/US2019/030684, International Preliminary Report on Patentability, Mailed on Nov. 19, 2020, 8 pages.
Application No. PCT/US2019/030684, International Search Report and Written Opinion, Mailed on Jun. 25, 2019, 11 pages.
Application No. PCT/US2019/030691, International Preliminary Report on Patentability, Mailed on Nov. 19, 2020, 12 pages.
Application No. PCT/US2019/030691, International Search Report and Written Opinion, Mailed on Sep. 23, 2019, 15 pages.
Application No. PCT/US2019/030691, International Search Report and Written Opinion, Mailed on Dec. 5, 2019, 18 pages.
PCT/US2019/030691, "Invitation to Pay Additional Fees and, Where Applicable, Protest Fee", Jul. 30, 2019, 11 pages.
Application No. PCT/US2020/027920, International Preliminary Report on Patentability, Mailed on Oct. 21, 2021, 8 pages.
Application No. PCT/US2020/027920, International Search Report and Written Opinion, Mailed on Jul. 24, 2020, 10 pages.
Russell et al., "Artificial Intelligence: A Modern Approach", 2nd Edition, 2003, 145 pages.
China Appl. No. 202080032482.2, Office Action, Dec. 30, 2024, 8 pages.
Europe Appl. No. 19724681.2, Intention to Grant, Jan. 7, 2025, 8 pages.
Europe Appl. No. 19727552.2, Intention to Grant, Dec. 12, 2024, 8 pages.
U.S. Appl. No. 18/302,497, Non-Final Office Action, Dec. 6, 2023.
China Appl. No. 201910371922.6, Office Action, Oct. 11, 2023.
China Appl. No. 201910372761.2, Office Action, Jun. 29, 2023.
Europe Appl. No. 19724681.2, Office Action, Jul. 19, 2023.
China Appl. No. 201910372761.2, Office Action, Dec. 26, 2023.
U.S. Appl. No. 18/302,497, Non-Final Office Action, Dec. 19, 2024, 17 pages.
China Appl. No. 201910371922.6, Notice of Decision to Grant, Oct. 17, 2024, 7 pages.
U.S. Appl. No. 16/383,337, Notice of Allowance, Mailed on Jan. 23, 2023, 14 pages.
U.S. Appl. No. 18/302,497, Final Office Action, Jul. 1, 2024, 15 pages.
China Appl. No. 201910371922.6, Office Action, Feb. 29, 2024, 8 pages.
China Appl. No. 201910371922.6, Office Action, May 30, 2024, 9 pages.
China Appl. No. 202080032482.2, Office Action, Jul. 3, 2024, 9 pages.
Europe Appl. No. 19727552.2, Office Action, May 3, 2024, 8 pages.
U.S. Appl. No. 16/383,337, Corrected Notice of Allowability, dated Apr. 27, 2023.
China Appl. No. 202080032482.2, Office Action, dated Apr. 16, 2025.
Europe Appl. No. 20787437.1, Intention to Grant, Apr. 3, 2025.

* cited by examiner

SENSING PHYSIOLOGICAL PARAMETERS THROUGH AN ARTICLE

CROSS-REFERENCE TO RELATED APPLICATIONS

This application is a continuation of U.S. patent application Ser. No. 16/841,129 filed Apr. 6, 2020, which claims priority under 35 U.S.C. § 119 to U.S. Provisional Patent Application No. 62/833,362, filed on Apr. 12, 2019, the contents of both of which are hereby incorporated by reference in their entirety.

FIELD

The present application generally relates to sensing physiological parameters. In an example, an optical transmitter and an optical sensor placed outside an article (e.g., a diaper) are used to determine a heart rate and a respiratory rate by pulsing light through the article and measuring the returned light.

BACKGROUND

Solutions exist for measuring a heart rate and a respiratory rate of humans. For example, some solutions can detect a changing color of skin and derive a heart rate or respiratory rate therefrom by using a light source and an optical receiver that are placed directly on the skin.

But placing a sensor on skin may not be ideal. For example, an infant may not be comfortable with a sensor being on his or her skin for an extended period of time.

Additionally, when the wearer of the sensor is moving, existing solutions may obtain erroneous measurements or not be able to obtain measurements at all. For example, when the wearer of the sensor is moving, a received optical signal may be weak or unmeasurable due to sensor misalignment.

Hence, new solutions are needed.

SUMMARY

Various examples are described for detecting heart rate and respiratory rate. In an aspect, a sensor application obtains a set of measurements of light. For each measurement, the sensor application causes a light source to transmit a pulse of light through an article to an area of skin and determines a measurement of light returned from the article. The sensor application further determines, from the set of measurements of light, a periodic change in an amplitude of the returned light. The sensor application further identifies the periodic change in amplitude as a heart rate having an identical periodicity.

In another aspect, the sensor application determines a rate of change of the periodic change in amplitude or an envelope modulation of the set of measurements of light. The sensor application identifies a respiratory rate as equal to the rate of change. These illustrative examples are mentioned not to limit or define the scope of this disclosure, but rather to provide examples to aid understanding thereof. Illustrative examples are discussed in the Detailed Description, which provides further description. Advantages offered by various examples may be further understood by examining this specification.

BRIEF DESCRIPTION OF THE DRAWINGS

Features, embodiments, and advantages of the present disclosure are better understood when the following Detailed Description is read with reference to the accompanying drawings.

DETAILED DESCRIPTION

Figure 1:
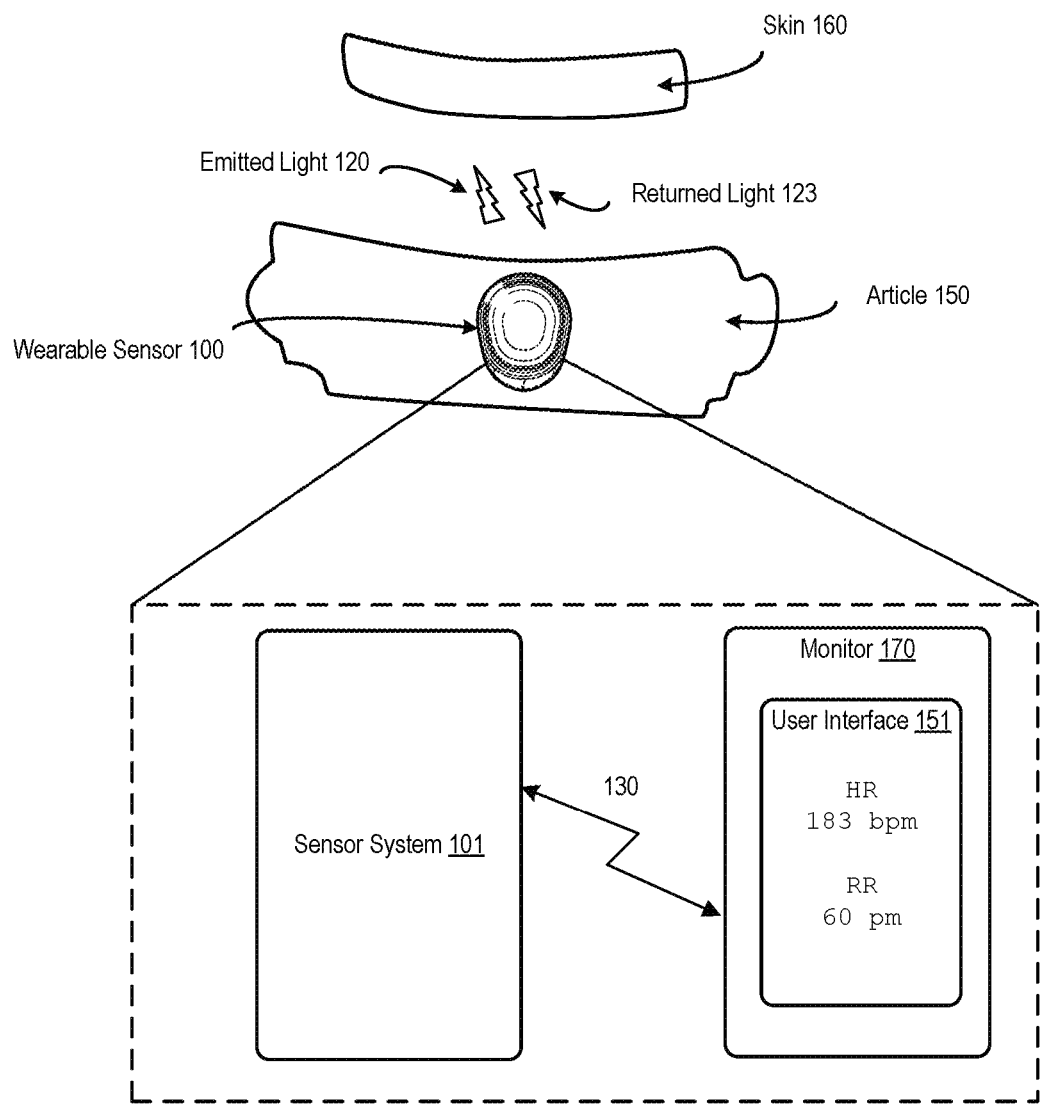
FIG. 1 depicts a block diagram of an example of a physiological sensor system according to certain aspects of the present disclosure.

Aspects described herein involve sensing physiological parameters. Examples of physiological parameters are heart rate and respiratory rate (respiratory rate). As mentioned above, existing systems can require a sensor to be placed on the skin. In contrast, disclosed solutions do not need to be placed directly on skin to detect a heart rate or breathing rate. Examples of articles include clothing, bedding, blanket, absorbent articles such as diapers.

In an example, a sensor application pulses a light source through an article onto skin, measures the returned light via a light receiver, and derives a heart rate and/or respiratory rate from the measurement of returned light. The wavelength, and therefore the color, of the light source can be selected to match a particular level of optical transmissivity for a particular article and/or to ensure a suitable amount of returned light to the light receiver for a color change of blood underneath skin to be discerned. Optical transmissivity is a measure of how much light is transmitted through material in relation to an amount of light incident on the material, and is wavelength-dependent.

In some cases, a sensor can be placed on a patch of the diaper with higher transmissivity.

Additionally, disclosed solutions can minimize a number of sensors that are needed to measure different parameters. For example, color-sensing devices disclosed herein can be used for detecting a change in color beneath the skin (and therefore to detect heartrate and/or respiratory rate) and can be dynamically be reconfigured to detect a color of a color strip on or within the diaper (therefore detecting a presence of volume of bodily exudate). The color strip can be located on the diaper. In this manner, disclosed solutions can be employed in existing systems, or can be deployed as multi-purpose systems.

In an aspect, different arrangements, or geometries, of light source and light receiver combinations can be available and selected. Having an array of light sources and light receivers facilitates dynamically selecting a light source-light receiver pair, or a geometry, that provides an optimal signal. In this manner, disclosed systems can adjust to movement caused by the wearer, or different thicknesses of diapers caused by moisture, e.g., urine, in the diaper. For example, if a diaper becomes full, then the diaper may become thicker. Disclosed systems can compensate by changing a geometry of the pulsed light with respect to a light receiver, thereby compensating for the increased light path due to the thicker absorbent material and continue to measure heart rate and/or respiratory rate.

In a further aspect, measurements obtained from other sensors such as wetness sensors and accelerometers are used to validate a heart rate or respiratory rate detected via the optical sensor. For example, by detecting and measuring motion of a wearer by using an accelerometer, disclosed systems can compensate for motion, enabling a continued measurement of heart rate and/or respiratory rate.

In yet another aspect, disclosed systems can supplement a determined activity state of a wearer (e.g., whether an wearer is feeding, sleeping, or is awake) with information determined by heart rate or respiratory rate. For example, if an infant is not moving, inertial measurement-based solutions may erroneously determine that the infant is sleeping. But by combining inertial measurements with respiratory rate determined via optical measurements, disclosed solutions can determine that a heart rate and/or respiratory rate remains elevated, indicating that the infant is not asleep but rather feeding. In another example, by determining that a heart rate and/or respiratory rate is consistent with sleep, disclosed solutions can discern that a wearer is asleep even in the presence of inertial measurements that indicate the wearer is moving (and therefore in some cases might otherwise indicate that the wearer is awake). For example, a wearer could be asleep in a moving car.

Turning now to the figures, FIG. 1 depicts a block diagram of an example of a physiological sensor environment according to certain aspects of the present disclosure. FIG. 1 depicts wearable sensor 100, article 150, emitted light 120, returned light 123, and skin 160. Examples of article 150 include clothing and absorbent articles such as a common disposable diaper, pantiliner, adult diaper, etc.

Wearable sensor 100 can be placed on an article or otherwise attached to a wearer. When properly located, one or more sensors housed inside the wearable sensor 100 can measure one or more parameters of the wearer. Wearable sensor 100 can be affixed to a wearer using an attachment device such as loops, hooks, or an adhesive. For example, wearable sensor 100 by using optical methods, inertial sensors, or both, can be configured to measure heart rate, respiratory rate, or both.

Wearable sensor 100 includes sensor system 101, network connection 130, and monitor 170. Sensor system 101 includes one or more light sources such as Light Emitting Diodes (LEDs) and one or more optical receivers such as photodiodes. Wearable sensor 100 can be placed on a diaper such that the light sources and optical receivers are aligned with a particular area of the diaper such as a color changing strip or a translucent portion of the diaper. Different arrangements of light sources and photodiodes are possible. Some examples are discussed further with respect to FIGS. 2-4 and 7.

Sensor system 101 and monitor 170 can be connected by network connection 130. Network connection 130 can be any wired or wireless connection. Examples include WiFi and Bluetooth. Any split of functionality between sensor system 101 and monitor 170 is possible. Therefore, sensing and analysis operations can be performed by sensor system 101, monitor 170, or both. For example, sensor system 101 can transmit a detected heart rate and/or a detected respiratory rate via network connection 130, to monitor 170. Monitor 170 can display information such as heart rate, respiratory rate, sleep state, and so on, to a caregiver. In an example, a heart rate is measured in beats per minute and respiratory rate is measured in breaths per minute.

In a more detailed example, sensor system 101 emits a pulse of emitted light 120. A pulse is an amount of light emitted for a specific amount of time. Emitted light 120 can shines through article 150, which absorbs some of emitted light 120. Some of emitted light 120 is transmitted to the skin 160. In turn, a portion this light is reflected back from skin 160 through the article 150 and is received as returned light 123. A light sensor (e.g., a photodetector or photodiode) in sensor system 101 receives the returned light 123.

Sensor system 101 samples the returned light 123 at a sampling rate, which can be adaptive or fixed. In some cases, multiple samples can be taken during one pulse of light. In other cases, one pulse causes one sample to be taken. With a sufficient number of samples, e.g., at a sampling rate sufficient to overcome aliasing, the sensor system 101 determines an amplitude of the returned light 123 over time. A signal or waveform is formed from set of samples. Sensor system 101 can pulse light on a duty cycle. An example duty cycle is one pulse every 100 milliseconds. The selected duty cycle can affect battery life. For example, more frequent light emission can use more battery power than an infrequent pulse of light.

The amplitude of returned light 123 can be periodic in nature based on a beating of the heart. More specifically, the amplitude of the light can vary over time, reflecting the fact that human skin absorbs different amounts of light at different points in the heart beat cycle. The absorption of specific wavelengths of light can differ based on blood pulse wave. For example, when the pulse wave arrives at the sensing location, a different amount of light is absorbed than when the pulse wave leaves, which results in a different amount of reflected light that is in turn measured.

More specifically, the received signal can include a fundamental component and one or more harmonic components. The periodicity of the fundamental component indicates the period of the heart rate. In some cases, the light can be filtered such that only a specific wavelength of light is considered.

From the detected heart rate, the sensor system 101 can determine a respiratory rate. Different methods can be used. For example, the sensor system 101 can determine that the heart rate increases slightly and then decreases slightly on a periodic basis. This period is the respiratory rate. Hence, the second time derivative of the received amplitude of light over time is the respiratory rate.

In another example, the sensor system 101 can analyze modulation of an envelope of the optical signal. For example, because respiration changes stroke volume and thus the pulse wave amplitude, the envelope of the optical signal modulates accordingly.

Sensor system 101 can include one or more inertial measurement sensors such as accelerometers or gyroscopes. These inertial sensors can determine inertial measurements that can supplement heart rate or respiratory rate measurements. Sensor system 101 can also include one or more wetness sensors. Additionally or alternatively, sensor system 101 can include one or more microprocessors.

A determined heart rate and/or respiratory rate can be combined with inertial measurement sensors to improve reliability of measurements. For example, sensor system 101 can determine that a wearer of a sensor is moving, and use the movement measurements to compensate for errors received in the returned light. Sensor system 101 can also use inertial measurements to determine a state of a wearer, for example, in conjunction with a predictive model.

Figure 2:
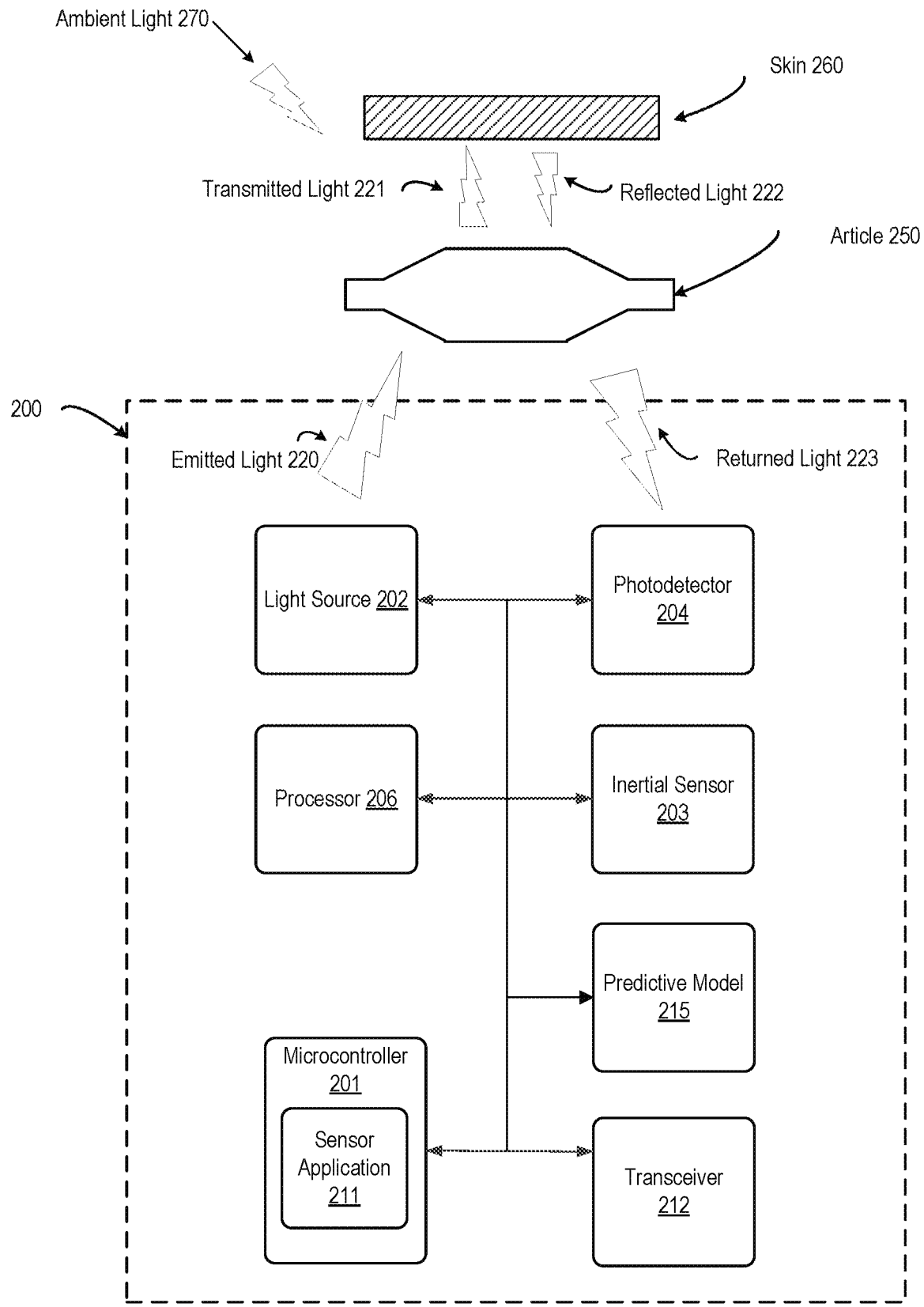
FIG. 2 depicts a block diagram of an example of a physiological sensor system, according to certain aspects of the present disclosure.

FIG. 2 depicts a block diagram of an example of a physiological sensor system, according to certain aspects of the present disclosure. FIG. 2 includes wearable sensor system 200, which is an example of sensor system 101. Wearable sensor system 200 includes one or more of microcontroller 201, light source 202, inertial sensor 203, photodetector 204, predictive model 215, and processor 206. Microcontroller 201 can execute sensor application 211. Wearable sensor system 200 can perform a variety of functions such as heart rate detection or activity state detection.

For example, wearable sensor system 200 can be configured to measure a color of skin to derive a heart rate or a respiratory rate. The detected color can be correlated with a pulse of a heart. A change in heart rate can be correlated with respiratory, thereby enabling a determination of a respiratory rate.

To detect color, wearable sensor system 200 causes a pulse of light to be emitted and determines the amount of the pulsed light that is reflected. Color sensing can occur including in the presence of ambient light 270, because wearable sensor system 200 can remove a measurement of the ambient light from the measurement.

In an example, sensor system 101 emits emitted light 220. Emitted light 220 can be a pulse, e.g., a light emitted for a specific amount of time. Emitted light 220 shines on article 150. Article 150 absorbs some of emitted light 220 and transmits some of the emitted light 220 as transmitted light 221. Transmitted light 221 is transmitted to skin 160. In turn, a portion of transmitted light 221 is reflected back from skin 160 as returned light 222. A portion of returned light 222 passes through article 150 as returned light 223.

Continuing the example, a light receiver (e.g., a photodetector) in sensor system 101 receives the returned light 223. The sensor system 101 samples the returned light 223 at various points in time to determine a periodicity of the amplitude of the returned light 223. This periodicity can indicate a heart rate due to skin 160 absorbing different amounts of light depending on a time relative to a heartbeat. Hence, the first derivative of the received amplitude of light over time is the respiratory rate.

In another example, wearable sensor system 200 measures a color of a color changing indicator in an absorbent article. From the color, wearable sensor system 200 determines a loading of the absorbent article. Color changing indicators are designed to change color in response to contact with a substance having a particular property, such as a pH level. Examples include be Bromocresol green, which changes color based on the pH of a liquid to which the color changing indicator has been exposed. Other color changing indicators can be used. The detected pH level can be correlated with a volume of bodily exudate, because the pH level changes as the volume of bodily exudate in the absorbent article changes. Accordingly, a lookup table or function may be used to determine a volume for a given pH level, or color of the color changing indicator.

Figure 8:
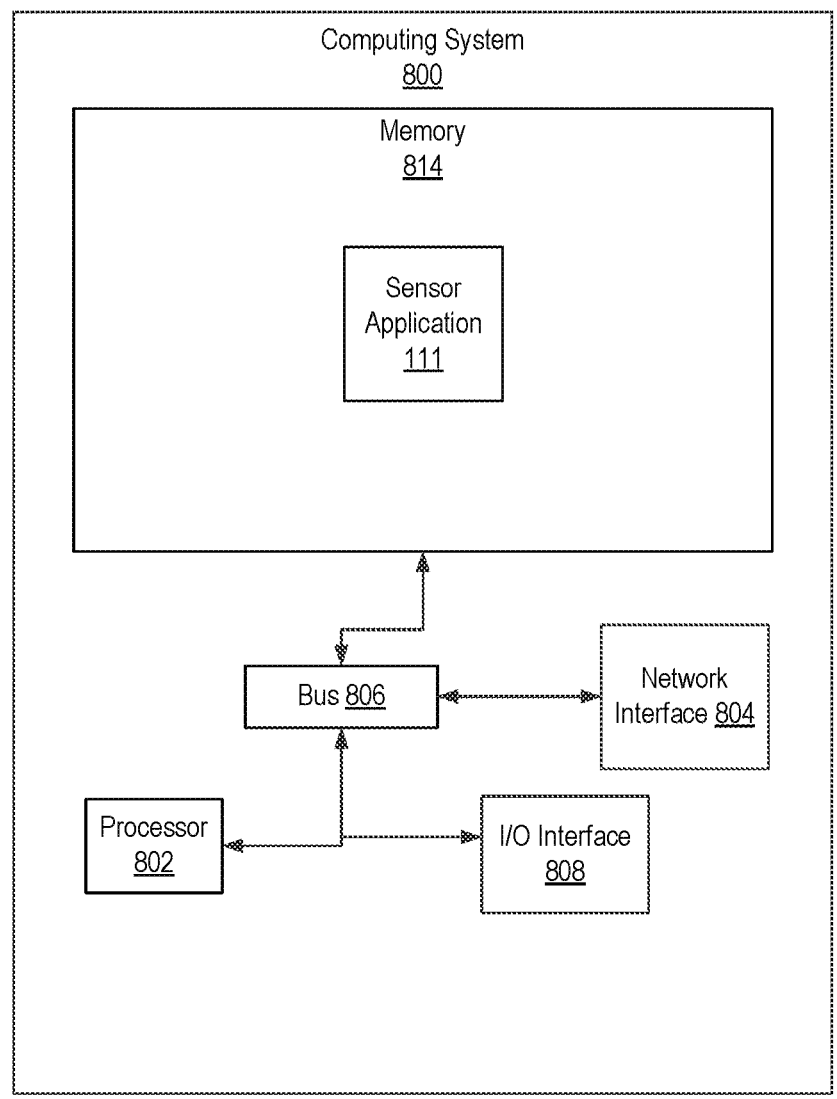
FIG. 8 is a diagram depicting an example computing system for performing functions related to sensing, according to certain aspects of the present disclosure.

Wearable sensor system 200 also includes a microcontroller 201. Microcontroller 201 can be any controller, processor, application specific integrated circuit or other processing device. An example of a computing device is shown in FIG. 8. Microcontroller 201 can execute sensor application 211 as well as other processor-executable instructions to perform aspects of the present disclosure. The functions of microcontroller 201 can be implemented by processor 206 or vice versa. Microcontroller 201 can store data, which can include a state of a wearer, demographic information about a wearer, information about a particular absorbent article worn by a wearer, and so forth.

Ambient light 270 can be any kind of light present in an environment that is not generated by light source 202, which can include light from natural sources, e.g., sunlight, or artificial light such as light created via incandescent light sources, halogen light sources, light emitting diode ("LED") light sources, fluorescent light sources, laser sources, etc. Even though ambient light can have different color spectra depending on the ambient light source(s) present, wearable sensor 100 can electronically remove the contribution of such ambient light to light detected by the photodetector and accurately detect the color of skin 260 based on returned light from the light source 202.

Light source 202 includes one or more light sources operable to shine light on skin 260. The light sources can be any suitable artificial light source according to this disclosure, including LEDs, incandescent light sources, or other light sources. Multiple discrete light sources can be implemented individually or via an integrated package that combines multiple individual light sources into a single light source.

Light from light source 202 can be generated at one or more specific wavelengths, or can encompass multiple wavelengths. In an example, light source 202 has three sources of light: red light at wavelength 623 nanometers ("nm"), green light at wavelength 523 nm, and infrared light at 700-nm to 1 mm wavelength. For example, for measuring a color of blood beneath human skin, wavelengths in the red, green, or infrared wavelengths may be advantageous. In some cases, infrared light can be preferred as it is not affected by skin color, therefore the reflected light more closely follows the pulse wave underneath the skin.

Other wavelengths of light may be employed according to different examples, depending on the application, the expected color range of a target object or color changing indicator such as a strip of litmus paper, expected ambient light spectra, or any other suitable factor. In some examples, the light source may be tunable to allow selection of a wavelength or wavelengths of light having a small contribution from the ambient light. For example, if ambient light detected by the photodetector indicates a local or global maximum or minimum magnitude at a first wavelength, the wearable sensor 100 can tune the light source 202 to emit light substantially at the first wavelength.

In this example, the wearable sensor system 200 pulses the light emitted by light source 202 by activating for a short duration, e.g., 1-5 microseconds to 500 milliseconds, called a "pulse width," and then deactivating the light source. Any suitable pulse width may be employed for a particular application. Light source 202 can create a separate pulse for red, infrared, and green, and output the corresponding values. For example, a pulse width of 5 microseconds may be advantageous to detect a color of a color changing indicator or a color of human skin. Short pulse widths enable the wearable sensor system 200 to pulse and detect different colors of light, e.g., red, green, and infrared, in quick succession of each other.

The use of pulsed light enables wearable sensor system 200 to disambiguate the type of light reflected by the object.

Specifically, wearable sensor system 200 can detect and filter the ambient light from detected light that includes light pulsed from the light source 202. In some examples, the wearable sensor system 200 can pulse the light source 202 at regular intervals, e.g., every ten minutes, or in response to an event, such as a user pressing a button on the wearable sensor system 200 or a humidity sensor detecting a humidity level exceeding a threshold. Additionally, the use of pulsed light as compared to continuous light can lower the power consumption of wearable sensor system 200, thereby increasing the amount of time that the wearable sensor system 200 can operate from a battery.

When the light source 202 is pulsed, the detected light at photodetector 204 may be a combination of ambient light 270 and light from the pulsed light source 202 reflected from the skin 260. When the light source 202 is inactive, the light detected by the photodetector 204 is ambient light. By pulsing the light source 202, wearable sensor system 200 is able to first obtain baseline information about the ambient light spectrum to enable the wearable sensor system 200 to isolate light received when the light source 202 is active. Pulsing also allows the wearable sensor 100 to save power by deactivating the light source 202 when a color measurement is not being taken.

Photodetector 204 receives a light, including light reflected from the skin 260, whether ambient light or light emitted by the light source 202, and generates sensor signals based on that returned light. Photodetector 204 can be any device that can detect and measure light such as a photodiode, phototransistor, complementary metal-oxide-semiconductor (CMOS) image sensor, charge-coupled device (CCD) sensor, or a photo-resistor.

Photodetector 204 can detect a wide spectrum of light and output information that indicates the detected light. For example, photodetector 204 can create an electrical output that is proportional to the wavelength of the returned light. Photodetector 204 can provide three outputs of a triplet, e.g., a value that corresponds to red, another value for green, and another value for infrared.

More specifically, the values of the triplet correspond to the amplitude of light at a range of wavelengths corresponding to a particular color. Therefore, a first value is proportional to an amplitude of red in the returned light, a second value is proportional to an amplitude of green in the returned light, and a third value is proportional to an amplitude of infrared in the returned light.

In an aspect, a photodetector 204 can be an array of individual photodetectors. Each photodetector can be configured to measure a color of light. For example, one photodetector measures red, a second photodetector measures infrared, and a third photodetector measures green.

Processor 206 is an electronic circuit or device such as a general-purpose processor. Processor 206 can operate in the analog domain, digital domain, or both. Processor 206 can discern the color of blood that is beneath the skin 260 independent of any ambient light. Processor 206 receives a first output from photodetector 204 that represents the ambient light, for example, an output gathered when the light source 202 is off. Processor 206 receives a second output from photodetector 204 when the light source 202 is pulsed. Processor 206 discerns a difference between the first output and the second output and thereby isolates the color of the object, specifically the color of the reflected light on the object from the pulsed light.

In an aspect, processor 206 receives a level indicating an intensity of broad spectrum light that represents the ambient light, i.e., the point in time that the light source 202 is off, and a level indicating the intensity of for a second point in time at which one of the three colors red, infrared, and green, is pulsed. Processor 206 can then disambiguate the contribution of the single pulsed color from the ambient light by comparing the intensity of the ambient light and the intensity with the single pulsed color.

Processor 206 receives a first set red, green, and infrared levels from photodetector 204 for a point in time that the light source 202 is off and a second set of red, green, and infrared levels from a second point in time that the light source 202 is pulsed. Processor 206 calculates a difference between the level of red between the first and second points in time, thereby calculating a contribution of red, green, and infrared levels from the pulsed light.

Processor 206 may be a specialized photometric front end. Processor 206 may be configured to activate light source 202 and measure a signal received by photodetector 204. For example, processor 206 can receive an analog input from photodetector 204, convert the analog input to a digital output by using a analog-to-digital converter (ADC), then store a numerical value indicating the detected color in an internal memory for later comparison with another value. In this manner, processor 206 may be configured to disambiguate the contribution of the ambient light 270 in the analog domain and output an analog signal or digital value indicative of the color of blood beneath the skin 260. For example, the processor 206 can provide an output, such as an triplet value representing the color.

In an aspect, processor 206 can have multiple detection channels, each corresponding to a pair that of a light source 202 and a photodetector 204. As described further with respect to FIGS. 3A and 3B, each channel can be dedicated to a specific light source-photodetector pair, or a "cell." Each cell can be physically separated so that the processor 206 may measure color in multiple places. Processor 206 can also pulse the light from a particular cell differently from a light from another cell.

Sensor application 211 can provide additional functionality such as calibration or white balancing for the signal received from light source 202. For example, sensor application 211 can retrieve known values such as the detected values when a known color, e.g. represented by a white or gray card or object that is presented to photodetector 204. Sensor application 211 can adjust the received red, infrared, and green levels according to the known calibration values.

In an aspect, microcontroller 201 may be connected to a transceiver 212. Transceiver 212 may communicate according to any suitable wireless protocol, such as Bluetooth, WiFi, near-field communication, etc. Using transceiver 212, microcontroller 201 may transmit the color of the skin 260 or, if detecting bodily exudate in an absorbent article, notify an external device that an absorbent article has been soiled. Microcontroller 201 may transmit information to a remote device, such as a smartphone, smartwatch, or other wearable device, or a remote computer, such as a server, e.g., a cloud-based server, for further processing and analysis.

Microcontroller 201 can, via the transceiver 212, transmit the detected color from processor 206 to a remote server, which can perform any of the operations discussed herein, for example, relating to heart rate or respiratory rate detection.

Certain aspects can determine an activity state of a wearer of sensor system 101 or part thereof. More specifically, by using an inertial sensor, sensor system 101 can receive indications of movement and determine, from the movement, an activity state of an infant. Examples of states include resting, sleeping, stirring, awake, and feeding. In an example, monitor 170 receives sensor measurements such as acceleration and angular velocity from sensor system 101 provides the measurements to the predictive model 215 to determine an activity based on the received sensor measurements. In this example, the predictive model 215 is a state-machine or algorithm, but may be any suitable type of predictive model in different examples such as a machine learning model or a classification model.

Inertial sensor 203 can include one or more accelerometers or gyroscopes. Inertial sensor 203 can provide indications of a wearer's activity, respiratory rate, or orientation such as on which side an infant is nursing or bottle feeding. For example, using precise movements gathered from an accelerometer or a gyroscope, the sensor system 101 and/or the monitor 170 can distinguish activities being performed by a wearer. For example, the activity classification system can distinguish deep sleep from light sleep, whether the wearer is on its stomach versus on its back, or whether an infant is nursing. Further, certain aspects described herein can use predictive models to further refine the system's ability to determine activity. For example, an accelerometer can measure acceleration of the wearer in one or more dimensions. The output of an accelerometer can therefore be a three-dimensional triplet of numerical values corresponding to the x, y, and z directions.

Gyroscopes measure angular velocity. For example, a gyroscope can output a signal proportional to the angular velocity of the wearer. Angular velocity changes in the direction of a torque applied to the gyroscope. Accordingly, when an infant that is wearing the sensor system 101 rolls over, the gyroscope can detect an increase in angular velocity. When the infant stops rolling, the angular velocity returns to zero. The direction component of the angular velocity can be used in various ways. For example, the direction of the velocity can help indicate which side, e.g., left or right, stomach or back, the infant is positioned. Processor 206 can sample the gyroscope at specific instances in time and obtain the angular velocity on a periodic basis.

In some examples, wearable sensor system 200 can be integrated into a sensor package that can be detachable and removable from article 250. For example, the sensor package can be adhered to the article 250 to prevent the sensor package slipping, while allowing its removal. The sensor package can include the wearable sensor 100 and/or the wearable sensor system 200 and can be included within a flexible, impermeable package. For example, the sensor package can have a housing that can withstand bodily exudate and feces, and is sufficiently thin as to not cause discomfort to a wearer of the absorbent article. The sensor package may be fabricated with flexible substrate such as a thin plastic or fluoroelastomer.

The sensor package housing can include a material that is washable or can be wiped. For example, the sensor package can be inserted into an absorbent article or adhered to the inside of the absorbent article. The sensor package can also be inserted into a pocket or pouch inside the absorbent article. Such a pocket or pouch can be hermetically sealed, for example, in transparent plastic that allows light to pass through. The sensor package can also be permanently attached into an absorbent article and discarded after a one-time use. The sensor package can also be adhered to the outside of the absorbent article via velcro or similar material.

Figure 3A:
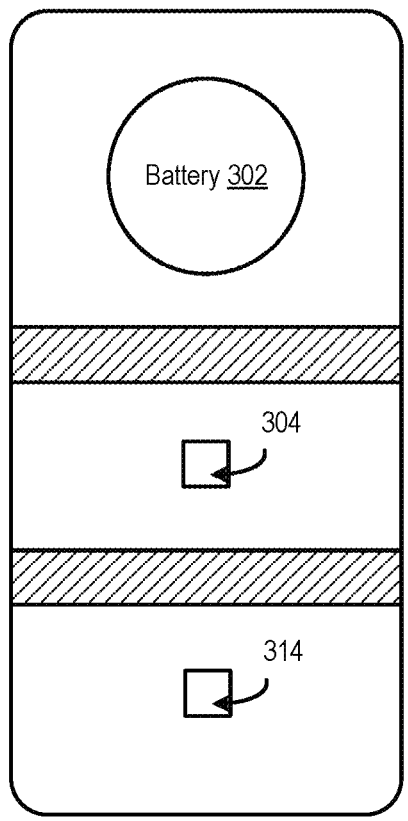
FIGS. 3A and 3B depict an example of a layout of a sensor system that can be placed in or on the outer surface of an article, according to certain aspects of the present disclosure.
Figure 3B:
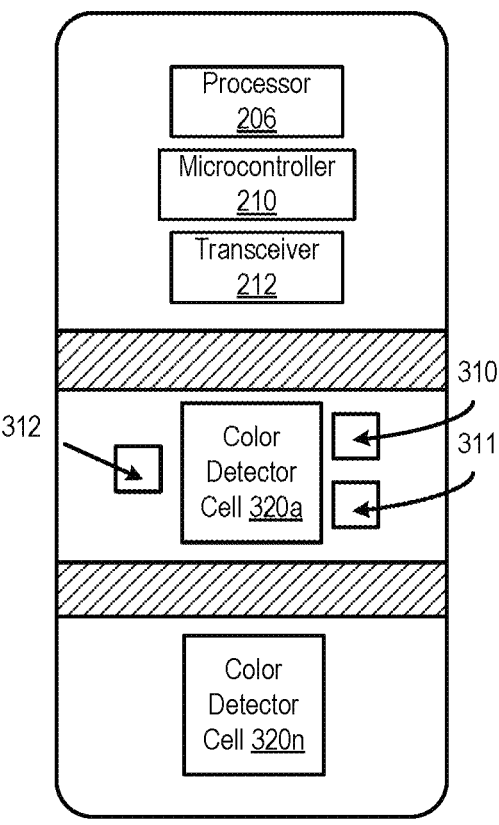

FIGS. 3A and 3B depict an example of a layout of a sensor system that can be placed in or on the outer surface of an absorbent article, according to certain aspects of the present disclosure. FIG. 3A represents a view of a first side of an exemplary a sensor layout for sensor package 300. FIG. 3B represents a view of a second side of an exemplary sensor layout for sensor package 300. The first and second sides are shown for example purposes; components can be placed on either the first or second side.

As depicted, the bottom is the side that is positioned to face and align with an object. Sensor package 300 includes a battery 302 and one or more color detector cells 320*a-n*. Sensor package 300 may also include a switch 304, electrical connectors (not depicted), a volatile organic compound ("VOC") sensor 310, a temperature sensor 311, a humidity sensor 312, an additional ambient light sensor 314, processor 206, microcontroller 201, or transceiver 212. Additional ambient light sensor 314 can be used in conjunction with the photodetectors to improve or augment the light detecting capability of sensor package 300. Some aspects may not include all of the components described above, or include variants thereof.

In addition, the sensor package 300 can cause an alarm, such as an audible beep. Accordingly, sensor package 300 can include a speaker or other audio output device. Sensor package 300 can also cause a transmission of an alert to another device, for example, operated by a caretaker. In another aspect, sensor package 300 can transmit an alert to another device. Sensor package 300 can include a transmitter or transceiver capable of transmitting a radio signal to an external device. Sensor application 211 operating on microcontroller 201 can also log events, such as a change in heart rate, to memory for later transmission to a caregiver.

Sensor package 300 can include one or more color detector cells 320*a-n*. For example, multiple color detector cells 320*a-n* can increase the ability of the sensor package 300 to detect changes in color through the absorbent article and/or a detection of color in multiple places.

Each color detector cell 320*a-n* includes a light source such as an LED and a photodetector such as a photodiode. In some aspects, as discussed further with respect to FIG. 4, a color detector cell may include multiple light sources or multiple photodetectors. Each color detector cell 320*a-n* detects light reflected by skin 260 such as a color strip, such as ambient light or pulsed light from the light source(s). The output of each color detector cell 320*a-n* is provided to a processor 206. The output of processor 206 can be provided to microcontroller 201. In some examples, each color detector cell 320*a-n* may have a dedicated processor 206, while in some examples, multiple color detector cells 320*a-n* may be connected to a common processor.

Sensor package 300 can include a switch 304 to activate or deactivate the sensor package 300. The switch 304 can be any suitable switch, such as a rocker-style on/off switch that connects the battery 302 to the electronics in sensor package 300 such as the color detector cells 320*a-n* and sensors 310-314. Switch 304 can also be a pushbutton switch that activates power from battery 302 to sensor package 300 for a period of time. Sensor package 300 can be configured to automatically turn off to save battery power. In an aspect, in conjunction with microcontroller 201, sensor package can be activated remotely. For example, a user can prompt an external device with a voice command, which causes the external device to transmit a request for a status of the absorbent article to the microcontroller 201 via a wireless connection, or a request to turn on or turn off the sensor package 300.

As discussed with respect to FIG. 2, processor 206 can discern a color of an object such as skin. Microcontroller 201 can execute an application such as sensor application 211 that can perform calibration of the detected color value.

Transceiver 212 can notify an external device if the sensor package 300 detects the presence of bodily exudate in an absorbent article.

In an aspect, sensor package 300 can also include a VOC sensor 310. VOC sensor 310 can detect the presence of volatile organic compounds such as feces from a bowl movement or VOCs present in blood. In conjunction with data obtained from color detector cells 320a-n, the VOC sensor 310 can provide additional information to microcontroller 201 based on one or more detected volatile organic compounds.

In an aspect, sensor package 300 can also include a temperature sensor 311. Temperature sensor 311 can detect heat from substances such as bodily exudate. In conjunction with data obtained from color detector cells 320a-n, the temperature sensor 311 can provide additional information such as a temporary increase in temperature to microcontroller 201. Because a notification of a temporary increase in temperature can indicate a presence of bodily exudate, such information can improve the accuracy and reliability of the detection.

In another aspect, sensor package 300 can also include a humidity sensor 312. Humidity sensor 312 can detect the presence of humidity, e.g., from bodily exudate. In conjunction with data obtained from color detector cells 320a-n, humidity sensor 312 can provide additional information such as a notification of a temporary increase in humidity to microcontroller 201. Because a temporary increase in temperature can indicate a presence of bodily exudate, such information can improve the accuracy and reliability of the detection.

As discussed, sensor package 300 can include multiple color detector cells 320a-n. The presence of more than one color detector cell 320a-n allows for increased accuracy and reliability. For example, one color detector cell 320a-n could become obstructed by an object, rendering detected values from that cell unusable, or because a thickness of the absorbent article can change based on a volume of liquid absorbed within, requiring the use of a different detector cell. In contrast, fewer color detector cells 320a-n can simplify the overall system architecture and may also lower power consumption. For example, in a system with three detector cells 320a-c, if one detector cell 320a returns a color measurement that is inconsistent with detector cells 320b and 320c, then microcontroller 201 can ignore the measurements from detector cell 320a.

Figure 4:
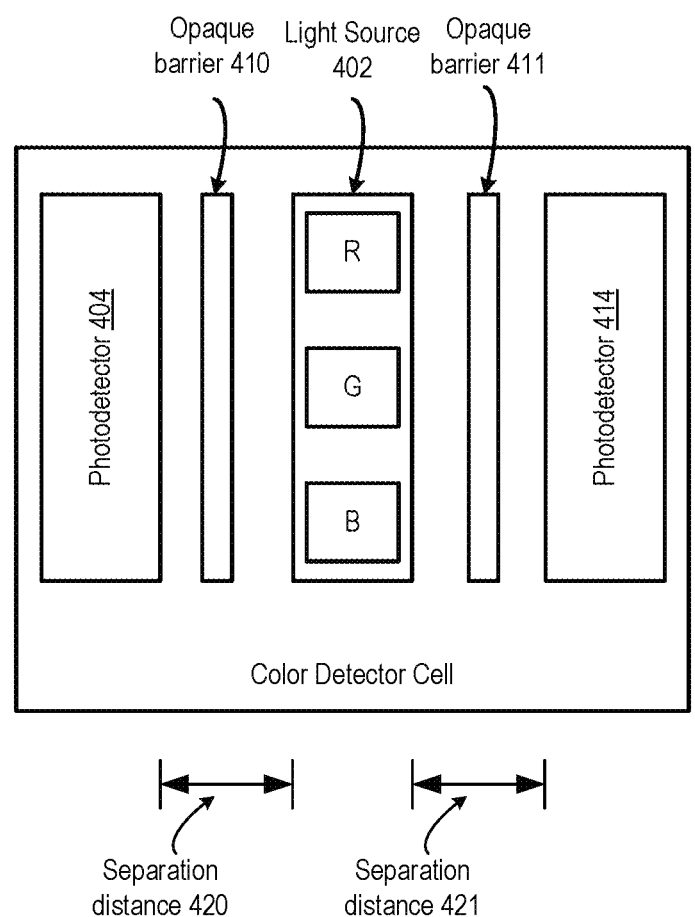
FIG. 4 depicts an example color detector cell configuration, according to certain aspects of the current disclosure.

FIG. 4 depicts an example color detector cell configuration, according to certain aspects of the current disclosure. As discussed, a sensor system such as sensor package 300 includes one or more color detector cells 320a-n. FIG. 4 shows an color detector cell 400 in more detail.

Color detector cell 400 includes two photodetectors, photodetector 404 and photodetector 414, light source 402, opaque barrier 410, and opaque barrier 411. Light source 402 can be any suitable light source according to this disclosure. As shown, light source 402 includes a red, an infrared, and a green light source, though different numbers and types of light sources 402 may be used according to different examples, which can allow the light sources can be turned on and off, i.e., pulsed, separately. Pulsing the light sources 402 that emit different colors separately allows color detector cell 400 to tailor the light output to a specific wavelength of light. For example, a particular color changing indicator may be more responsive to a specific wavelength of light at a specific pH level.

Photodetectors 404 and 414 can be any suitable photodetector according to this disclosure. Photodetectors 404 and 414 are connected to the processor 206. A separation distance 42 between the light source 402 and the photodetector 404 and separation distance 421 between light source 402 and photodetector 414 can be adjusted based on the application. In particular, the closer the light source 402 and a photodetector 404 or 414 are together, the greater the portion of light received at the photodetectors from the light source 402 (and less from ambient light 270). As an example only, separation distance 420 and separation distance 421 can be adjusted from 0.1 mm to 2 mm in separation. Other distances and configurations are possible. As a distance increases, all else being equal, the intensity of the light from the light source received at the photodetector decreases. Additionally, as the distance increases, the focal area being measured increases. As the distance decreases, the sensor is more focused on a smaller area directly under the sensor.

As shown, two photodetectors 404 and 414 are used. Photodetectors 404 and 414 can be positioned to be parallel to each other. In this configuration, the combination of photodetectors 404 and 414 provides a stronger output signal to the processor 206 than otherwise. Using more than one photodetector also provides an advantage in that error can be reduced if the sensor system is misaligned with respect to the object.

Color detector cell 400 can include one or more opaque barriers 410-411 positioned between the light source 402 and the photodetectors 404, 414. The opaque barriers 410-411 reduce the amount of light from light source 402 that travels directly to the photodetector 404 without reflecting off of the object. Opaque barriers 410-411 can be poron or similar material. In an aspect, the photodetectors 404 or 414 can include such an opaque barrier, or an opaque housing of the photodetector 404 or 414 can be extruded in such a manner that the opaque housing is located between the LED and photodiodes. In an aspect, the opaque barriers 410-411 are omitted to simplify the design.

Figure 5:
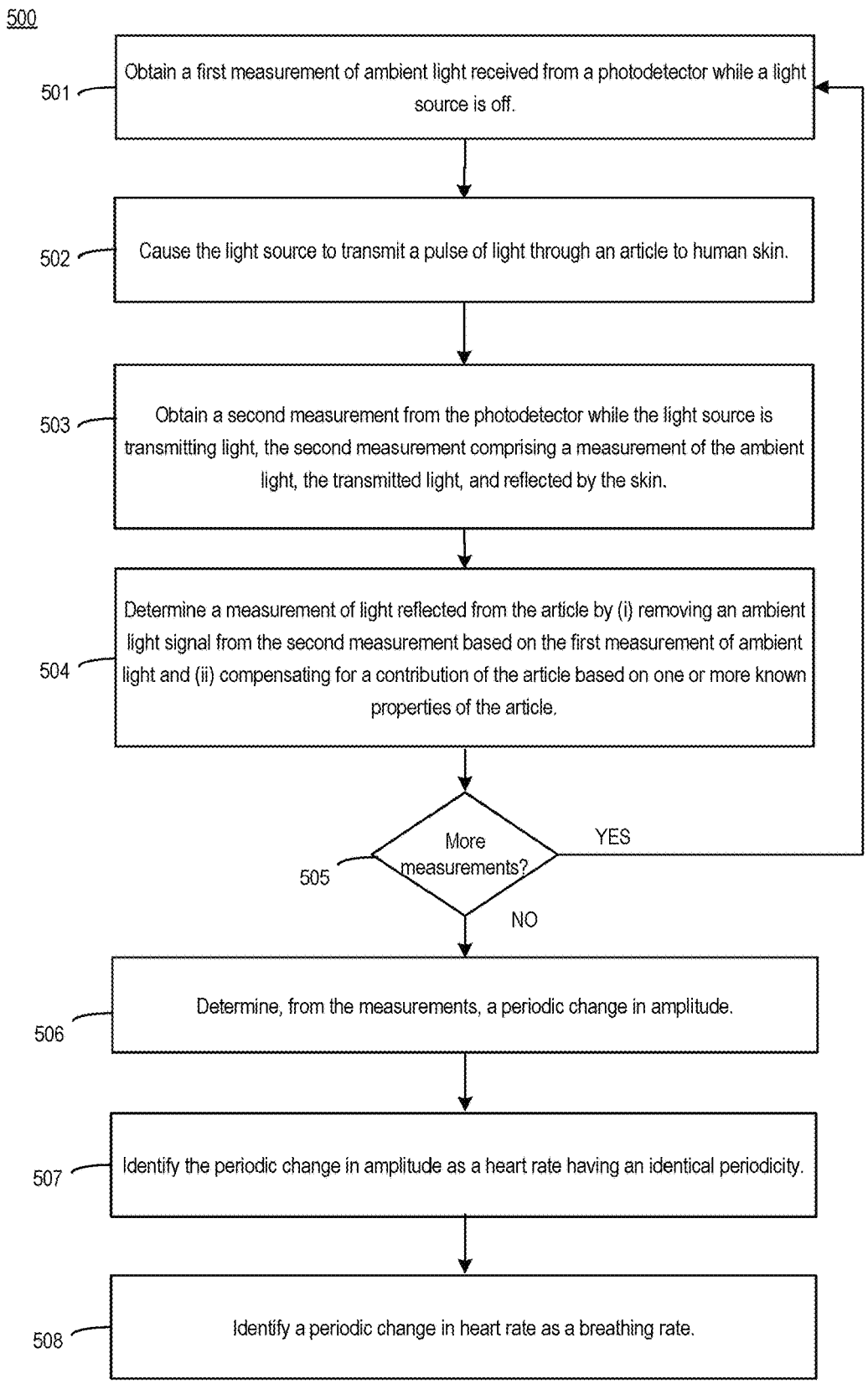
FIG. 5 is a flowchart that depicts an example of a method for determining physiological parameters through an article, according to certain aspects of the present invention.

FIG. 5 is a flowchart that depicts an example of a method 500 for determining physiological parameters through an absorbent article, according to certain aspects of the present invention. Method 500 involves obtaining a set of normalized measurements of light and then using those measurements to determine a heart rate and respiratory rate. For discussion purposes, method 500 is discussed as being performed by sensor application 211, but can be performed by any suitable computing device or application. As depicted in FIG. 3, more than one color detector cells 320a-n can be used. Therefore, such an aspect, method 500 may be performed with respect to each color detector cell 320a-n. More specifically, the photodetector in each color detector cell 320a-n can independently perform the blocks of method 500.

At block 501, method 500 involves obtaining a first measurement of ambient light received from a photodetector while a light source is off. Photodetector 204 detects the ambient light present and outputs a representation of the color of the light or a representation of an intensity of broad-spectrum light that is present. For example, photodetector 204 can create an electrical output that is proportional to the wavelength or the intensity of the returned light. In an aspect, the photodetector 204 can provide three outputs that each correspond to red, green, or infrared: a first that is proportional to an amplitude of red in the returned light, a second that is proportional to an amplitude of green in the returned light, a third that is proportional to an amplitude of infrared in the returned light.

Photodetector 204 provides the first measurement of light to the processor 206. In this example, the first light measurement is taken while a light source 202 is off and represents ambient light reflected from the skin 260. The first light measurement can represent an intensity of broad-spectrum light or an intensity of a specific wavelength of light.

At block 502, method 500 involves causing the light source to transmit a pulse of light through an article to human skin. Sensor application 211 causes light source 202 to transmit light on to skin 260. More specifically, processor 206 activates light source 202 for a predetermined pulse time interval.

In some examples, multiple light sources may be pulsed simultaneously or individually. For example, aspects using sensor package 300 may include more than one color detector cell 320a-n. The light source in each color detector cell 320a-n may be pulsed separately or together with the other light sources.

The wavelength of the light emitted by light source 202 can be adjusted based on the optical properties of the article 250. For example, different diapers can have different rates of optical transmissivity. Additionally, these rates can vary by emitted wavelength. For example, a diaper may allow transmission of more light at a first wavelength than at a second wavelength. Examples of suitable wavelengths include, green, red, and infrared. For example, benefits of green include a higher reactivity with water in human skin. Infrared also has advantages, such as being agnostic to skin tone, but has disadvantages such as being more sensitive to motion. In some cases, more than one wavelength can be used, for example by using multiple light sources and/or multiple light receivers. Further, as the absorbent material absorbs liquid, its optical property may change and the wavelengths can be selected to adjusted to the changing material.

In some cases, a specific wavelength or wavelengths are selected due to a specific article being present. For example different articles can react differently to different wavelengths of light.

At block 503, method 500 involves obtaining a second measurement from the photodetector while the light source is transmitting light, the second measurement comprising a measurement of the ambient light, the transmitted light, and reflected by the skin. More specifically, sensor application 211 obtains a second measurement from the photodetector during the transmission, the second measurement including the ambient light and the transmitted light reflected from the object. Processor 206 obtains a second measurement of light during the time interval that the pulse from light source 202 is on. The second measurement includes the ambient light and the light from the pulsed light source 202. In an aspect such as sensor package 300, the photodetector in each color detector cell 320a-n each obtains a second measurement of light. Sensor application 211 uses the first and second measurements to determine the color of an object.

At block 504, method 500 involves determining a normalized measurement of light reflected from an article by (i) removing an ambient light signal from the second measurement based on the first measurement of ambient light and (ii) compensating for a contribution of the article based on one or more known properties of the article.

Sensor application 211 determines a normalized measurement of the reflected light by removing an ambient light signal from the second measurement based on the first measurement. Removal can be performed in the analog domain or the digital domain.

For example, processor 206 subtracts the first measurement, representing the ambient light, from the second measurement, representing the ambient light combined with the reflected light from light source 202. The result of the subtraction is the light reflected from the skin 260, such as a color changing indicator. If operating in the digital domain, processor 206 converts the first measurement into a digital or numeric representation of the red, green, and infrared levels. Processor 206 converts the second measurement into a digital or numeric representation of the red, green, and infrared levels. Processor 206 computes a new red level by subtracting the first measurement from the red level of the second measurement, a new green level by subtracting the first measurement from the green level of the second measurement, and a new infrared level by subtracting the first measurement from the infrared level of the second measurement. The new red, green, and infrared levels represent the color of the light reflected from the object.

Sensor application 211 compensates for a contribution of the article based on one or more known properties of the article. In some cases, the material used can have an optical property that allows certain wavelengths to transmit more efficiently. This can be engineered by changing certain layer's thickness or by opening an aperture where light-blocking layers are removed.

At block 505, method 500 involves determining whether any more samples are needed. The sampling rate can be fixed or adaptive. At least several samples per heartbeat can be needed to avoid aliasing. Because a heart rate can be as high as 200 beats/minute, in some cases, therefore, sampling frequencies should be at least 20 Hertz to avoid aliasing. Additionally, a sufficient number of samples such that multiple periods are sampled can provide for further stability in measurement and for additional error correction.

At block 506, method 500 involves determining, from a set of measurements, a periodic change in amplitude. FIG. 5 is discussed with respect to FIG. 6, which illustrates exemplary waveforms associated with heart rate.

Figure 6:
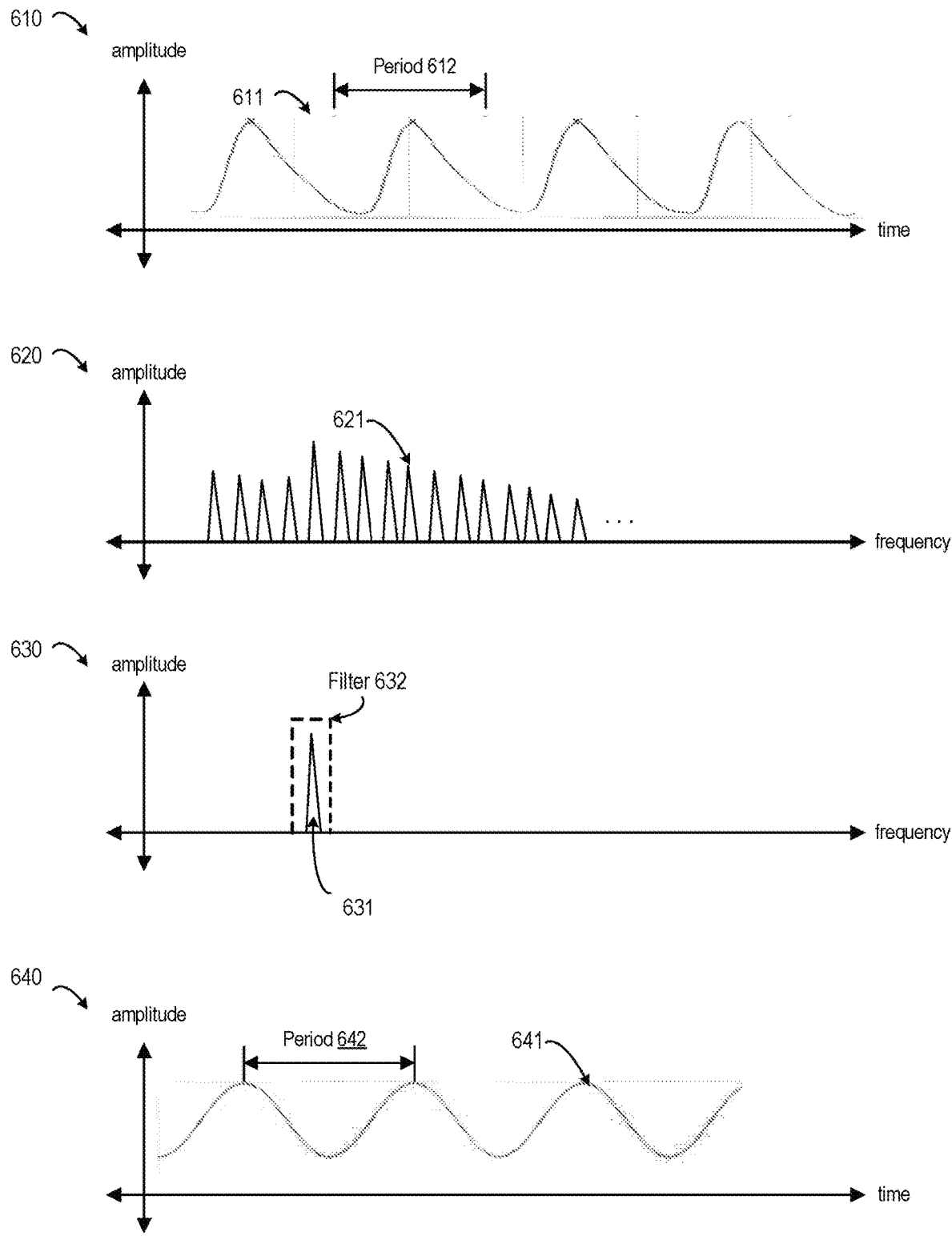
FIG. 6 depicts examples of waveforms associated with the method described in FIG. 5, according to certain aspects of the present invention.

FIG. 6 depicts examples of waveforms associated with the method described in FIG. 5, according to certain aspects of the present invention. FIG. 6 depicts four graphs: graph 610, graph 620, graph 630, and graph 640.

Graph 610 includes waveform 611, which is an example of a returned light signal. Waveform 611 represents an amplitude of returned light over time. As can be seen, waveform 611 is a sawtooth-like waveform. Waveform 611 can include a fundamental and one or more harmonics. Waveform 611 has period 612, which can be identified by sensor application 211.

At block 507, method 500 involves identifying the periodic change in amplitude as a heart rate having an identical periodicity. Period 612 can indicate a period of a heart rate. Different approaches can be used to determine the heart rate. For example, time domain approaches or frequency-domain approaches can also be used.

For example, by using a time-domain approach, sensor application 211 can identify either two minima or two maxima in waveform 611. Sensor application 211 determines a time between the two minima or two maxima. The period indicates the period of the heart rate, therefore heart rate=1/period. Graph 640 includes waveform 641, which represents a fundamental component of waveform 641 having period 642.

Waveform 641 can be identified in the time domain or the frequency domain. Frequency domain approaches involve identifying aptitude peaks for a specific frequency that matches the criteria of a heart rate. Sensor application 211 performs a Fourier transform on waveform 611, resulting in waveform 621. From waveform 611, sensor application 211 selects and analyzes a particular frequency component. Graph 620 includes waveform 621, which represents a frequency-domain representation of waveform 611.

Different criteria can be used for selecting the frequency component that indicates a heart rate. For example, the relevant frequency component can be the frequency component with the lowest frequency. In other cases, perhaps due to low-frequency noise, the relevant frequency component can be the component with the highest energy.

In some aspects, sensor application 211 checks multiple frequency components and before selecting the component, verifies that the component is reasonable (within an expected range) for a heart rate. This approach helps filter out data caused by noise. Heart rate can vary by age. For example, an infant's heart rate can be between 50-200 beats/min. For example, from 50 to 215 beats per minute. For example, a newborn infant can have a heart rate of 80-215 minutes but a school age child can have a heart rate between 60-140 beats per minute.

Continuing the example, graph 630 depicts waveform 631, which represents a filtered frequency-domain representation of waveform 621. Waveform 631 is filtered by filter 632. Filter 632 represents a band-pass filter around the peak that has the highest energy. Filter 632 can be a digital filter.

In an aspect, sensor application 211 can determine that an amplitude of a particular selected frequency is below a threshold, indicating that the signal is of insufficient quality. In this case, sensor application 211 can wait for a threshold amount of time and pulse the light source again and sample the returned light, or change to a different geometries.

At block 508, method 500 involves identifying a periodic change in heart rate as a respiratory rate. When a human is respiratory in, the heart rate goes up and when a human is respiratory out, the heart rate goes down slightly. Sensor application 211 can identify this change from the heartrate detected at block 507 with a sufficient amount of measurements. Different approaches can be used. Examples include detecting a modulation of heart rate or using an envelope of the waveform representing the returned light. For example, the envelope modulates at the frequency of the respiratory rate. By analyzing changes in the envelope, sensor application 211 determines a respiratory rate.

In yet another aspect, sensor application 211 can correlate a detected respiratory rate with sensor data from inertial measurements. For example, accelerometer data can indicate abdominal movement associated with respiration. If the abdominal movements do not correlate with the detected respiratory rate, then sensor application 211 can confirm the respiratory rate with an additional set of optical measurements, or take another action.

In another aspect, sensor application can combine respiratory rate with inertial sensor measurements to detect a stage of sleep of a wearer. Stages of sleep can include awake, asleep, and gradients in-between. For example, by providing predictive model 215 inertial measurement and respiratory data, predictive model 215 can determine when an wearer is transitioning from a first sleep stage a second sleep stage. Such a determination can be useful, for example, to warn caregivers to be especially quiet because a wearer may be more likely to wake up during the transition. In other cases, such determinations can help caregivers know when not to attend to a wearer so that the wearer can learn not to wake up when transitioning between sleep stages. Deep sleep can be identified by a reduced heart rate and respiratory rate.

In some aspects, different or multiple sources and optical receivers may be employed at different locations within the article to better detect heart rate and/or respiratory rate.

Configurations of light sources and optical receivers can be referred to as geometries. An example of a sensor configuration that facilitates multiple geometries is depicted in FIG. 7.

Figure 7:
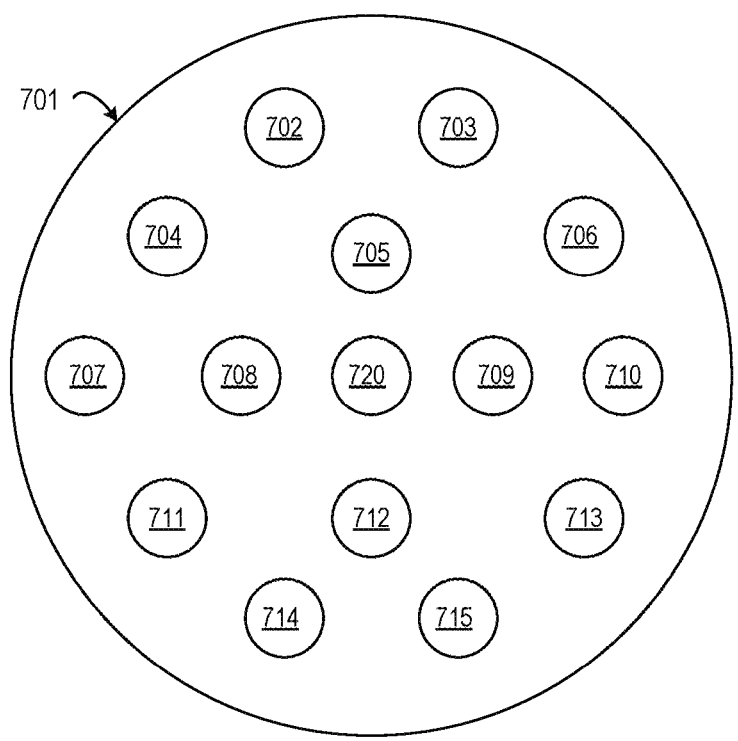
FIG. 7 depicts an example of a color detector cell configurable with different geometries, according to certain aspects of the present invention.

FIG. 7 depicts an example configuration a color detector cell configurable with geometries, according to certain aspects of the present invention. FIG. 7 depicts detector module 701, which includes light sources 702-715 and optical receiver 720. For example purposes, thirteen light sources and one receiver are shown. But any number of light sources and receivers are possible. Detector module 701 is placed on an article such that one or more of light sources 702-715 can shine through the article. Each light source or optical receiver can have a different optical filter and/or can be tuned for a different wavelength.

As can be seen, some light sources, e.g., light sources 702 and 715, are further away from optical receiver 720. Therefore, with respect to optical receiver 720, light sources 702 and 715 provide a greater radius of light than light sources closer to a center such as light source 709.

Sensor application 211 can select a suitable combination of light source and optical receiver by determining an amount of returned light and comparing the returned light to expected norms. For example, if no identifiable highest-energy frequency peak exists, then sensor application 211 determines there is too much noise, then sensor application 211 can select a light source and receiver pair that provides a highest signal quality.

In an aspect, sensor application 211 can also determine a volume or presence of moisture (e.g., urine) present in a diaper. Based on the determined volume, sensor application 211 can then select a different geometry due to thickness caused by moisture in the diaper. More specifically, if moisture is present, than then sensor application 211 may use a light source on an outer ring, e.g., light source 702 or 713. Conversely, if no moisture is present, then sensor application 211 may use a light source closer to the optical receiver 720, e.g., light source 709.

Color calibration can be performed on each light source and optical receiver pair. For example, sensor application 211 can convert the red, green, and infrared levels to hue, saturation, and lightness/value and perform calculations on the hue, saturation, and lightness/value. Color calibration can be implemented via a table. For example, for a given triple of red, green, and infrared, adjust the values by certain amount. Color calibration can also be performed in a different domain such as hue, saturation, and lightness, or hue, saturation, and value.

Motion Compensation

Aspects of the present invention can sense heart rate while a wearer is moving. By using measurements gathered from inertial sensor 203, sensor application 211 can determine that a wearer is moving, is not moving, or a specific level of movement. A determination of movement can be useful in multiple cases.

For example, if the wearer is moving, then light measurements may be incorrect. In this case, sensor application 211 can receive two streams of data, one from the optical receiver and another from the accelerometer. By using motion compensation, sensor application 211 can remove any motion artifacts from the optical waveform, thereby resulting in an accurate heart rate or respiratory rate measurement. This can be performed by analyzing common elements between the optical signal and the accelerometer signal, in either time domain or frequency domain, and subtracting this common element from the optical signal. For example, the optical signal may contain artifacts due to a baby swing. The accelerometer signal also contains the swing motion, and can provide the swing frequency. Then, the optical signal can remove signal contents of such frequency to eliminate the motion artifact.

In another example, if the wearer is asleep, then it may be expected that respiratory rates are lower. An inertial measurement sensor can independently verify respiratory rate while the wearer is asleep. For example, an inertial measurement sensor can obtain a set of samples from which a periodicity can be measured that corresponds to respiratory rate. This respiratory rate can be compared to a respiratory rate obtained via optical measurements.

FIG. 8 is a diagram depicting an example computing system for performing functions related to sensing, according to certain aspects of the present disclosure. Some or all of the components of the computing system 800 can belong to the microcontroller 210 or the processor 206 of FIG. 2. For example, the sensor application 211 may operate on the computing system 800. The computing system 800 includes one or more processors 802 communicatively coupled to one or more memory devices 814. The processor 802 executes computer-executable program code, which can be in the form of non-transitory computer-executable instructions, stored in the memory device 814, accesses information stored in the memory device 814, or both. Examples of the processor 802 include a microprocessor, an application-specific integrated circuit ("ASIC"), a field-programmable gate array ("FPGA"), or any other suitable processing device. The processor 802 can include any number of processing devices, including one.

The memory device 814 includes any suitable computer-readable medium such as electronic, optical, magnetic, or other storage device capable of providing a processor with computer-readable instructions or other program code. Non-limiting examples of a computer-readable medium include a magnetic disk, a memory chip, a ROM, a RAM, an ASIC, optical storage, magnetic tape or other magnetic storage, or any other medium from which a processing device can read instructions. The instructions may include processor-specific instructions generated by a compiler or an interpreter from code written in any suitable computer-programming language, including, for example, C, C++, C #, Visual Basic, Java, Python, Perl, JavaScript, and ActionScript.

The computing system 800 may also include a number of external or internal devices such as input or output devices. For example, the computing system 800 is shown with an input/output ("I/O") interface 808 that can receive input from input devices or provide output to output devices. A bus 806 can also be included in the computing system 800. The bus 806 can communicatively couple one or more components of the computing system 800 and allow for communication between such components.

The computing system 800 executes program code that configures the processor 802 to perform one or more of the operations described above with respect to FIGS. 1-7. The program code of the sensor application 111, which can be in the form of non-transitory computer-executable instructions, can be resident in the memory device 814 or any suitable computer-readable medium and can be executed by the processor 802 or any other one or more suitable processor. Execution of such program code configures or causes the processor(s) to perform the operations described herein with respect to the microcontroller 210. In additional or alternative aspects, the program code described above can be stored in one or more memory devices accessible by the computing system 800 from a remote storage device via a data network. The microcontroller 210 and any processes can use the memory device 814. The memory device 814 can store, for example, additional programs, or data used by the applications executing on the processor 802 such as the sensor application 111.

The computing system 800 can also include at least one network interface 804. The network interface 804 includes any device or group of devices suitable for establishing a wired or wireless data connection to one or more data networks. Non-limiting examples of the network interface 804 include an Ethernet network adapter, WiFi network, Bluetooth, or Bluetooth Low Energy (BLE), a modem, or the like. The computing system 800 is able to communicate with one or more other computing devices or computer-readable data sources via a data network using the network interface 804.

Numerous specific details are set forth herein to provide a thorough understanding of the claimed subject matter. However, those skilled in the art will understand that the claimed subject matter may be practiced without these specific details. In other instances, methods, apparatuses, or systems that would be known by one of ordinary skill have not been described in detail so as not to obscure claimed subject matter.

Unless specifically stated otherwise, it is appreciated that throughout this specification discussions utilizing terms such as "processing," "computing," "calculating," "determining," and "identifying" or the like refer to actions or processes of a computing device, such as one or more computers or a similar electronic computing device or devices, that manipulate or transform data represented as physical electronic or magnetic quantities within memories, registers, or other information storage devices, transmission devices, or display devices of the computing platform.

The system or systems discussed herein are not limited to any particular hardware architecture or configuration. A computing device can include any suitable arrangement of components that provide a result conditioned on one or more inputs. Suitable computing devices include multi-purpose microprocessor-based computer systems accessing stored software that programs or configures the computing system from a general purpose computing apparatus to a specialized computing apparatus implementing one or more aspects of the present subject matter. Any suitable programming, scripting, or other type of language or combinations of languages may be used to implement the teachings contained herein in software to be used in programming or configuring a computing device.

The foregoing description of some examples has been presented only for the purpose of illustration and description and is not intended to be exhaustive or to limit the disclosure to the precise forms disclosed. Numerous modifications and adaptations thereof will be apparent to those skilled in the art without departing from the spirit and scope of the disclosure.

That which is claimed is:

1. A method comprising:
   obtaining a first plurality of measurements of light, wherein obtaining the first plurality of measurements of light comprises, for each measurement:
   causing a first light source to transmit a pulse of light through an article to an area of skin, wherein the first light source is positioned in a first configuration; and
   determining a first measurement of light returned from the article;
   responsive to determining that an energy level of the first plurality of measurements of light is lower than a threshold obtaining, a second plurality of measurements of light, wherein obtaining the second plurality of measurements of light comprises, for each measurement:
causing a second light source to transmit a second pulse of light through the article to the area of skin, wherein the second light source is positioned in a second configuration that is different from the first configuration; and
obtaining a second measurement of light returned from the article;
determining, from the first plurality of measurements of light and the second plurality of measurements of light, a periodic change in an amplitude; and
identifying the periodic change in amplitude as a heart rate based on the periodic change in amplitude.

2. The method of claim 1, further comprising:
removing an ambient light signal from one or more of the first plurality of measurement of light and the second plurality of measurement of light.

3. The method of claim 1, further comprising:
obtaining, via an inertial measurement device, a plurality of data samples; and
responsive to determining that the heart rate is below a heart rate threshold, determining, from the plurality of data samples, that an infant wearing the article is asleep in a moving carrier.

4. The method of claim 1, further comprising:
determining a rate of change in one or more of (i) the periodic change in amplitude or (ii) an envelope modulation of the first plurality of measurements of light and the second plurality of measurements of light; and
identifying a respiratory rate as equal to the rate of change.

5. The method of claim 1, wherein identifying the periodic change in amplitude comprises:
obtaining a plurality of frequency components by transforming one or more of the first plurality of measurements of light and the second plurality of measurements of light into a frequency domain; and
identifying, from the plurality of frequency components, a component comprising a highest energy content.

6. The method of claim 1, wherein identifying the periodic change in amplitude comprises:
obtaining, via an inertial measurement device, a plurality of data samples;
determining that the plurality of data samples indicate movement of a wearer wearing the article;
correlating the plurality of data samples with one or more of the first plurality of measurements of light and the second plurality of measurements of light; and
removing, from one or more of the first plurality of measurements of light and the second plurality of measurements of light, a contribution of the movement.

7. The method of claim 1, further comprising:
adjusting one or more of the first plurality of measurements of light and the second plurality of measurements of light to compensate for a contribution of the article based on one or more known properties of the article.

8. A system comprising:
a non-transitory computer-readable medium storing computer-executable program instructions; and
a processing device communicatively coupled to the non-transitory computer-readable medium for executing the computer-executable program instructions, wherein executing the computer-executable program instructions configures the processing device to perform operations comprising:
obtaining a first plurality of normalized measurements of light, wherein obtaining the first plurality of measurements of light comprises, for each measurement:
causing a first light source to transmit a pulse of light through an article to an area of skin, wherein the first light source is positioned in a first configuration;
determining a first measurement of light returned from the article;
responsive to determining that an energy level of the first plurality of measurements of light is lower than a threshold obtaining, a second plurality of measurements of light, wherein obtaining the second plurality of measurements of light comprises, for each measurement:
causing a second light source to transmit a second pulse of light through the article to the area of skin, wherein the second light source is positioned in a second configuration that is different from the first configuration; and
obtaining a second measurement of light returned from the article;
determining, from the first plurality of measurements of light and the second plurality of measurements of light, a periodic change in an amplitude; and
identifying the periodic change in amplitude as a heart rate based on the periodic change in amplitude.

9. The system of claim 8, wherein executing the computer-executable program instructions configures the processing device to perform operations comprising:
removing an ambient light signal from one or more of the first plurality of measurement of light and the second plurality of measurement of light.

10. The system of claim 8, wherein executing the computer-executable program instructions configures the processing device to perform operations comprising:
obtaining, via an inertial measurement device, a plurality of data samples; and
responsive to determining that the heart rate is below a heart rate threshold, determining, from the plurality of data samples, that an infant wearing the article is asleep in a moving carrier.

11. The system of claim 8, wherein executing the computer-executable program instructions configures the processing device to perform operations comprising:
determining a rate of change in one or more of (i) the periodic change in amplitude or (ii) an envelope modulation of the first plurality of measurements of light and the second plurality of measurements of light; and
identifying a respiratory rate as equal to the rate of change.

12. The system of claim 8, wherein identifying the periodic change in amplitude comprises:
obtaining a plurality of frequency components by transforming one or more of the first plurality of measurements of light and the second plurality of measurements of light into a frequency domain; and
identifying, from the plurality of frequency components, a component comprising a highest energy content.

13. The system of claim 8, wherein identifying the periodic change in amplitude comprises:
obtaining, via an inertial measurement device, a plurality of data samples;
determining that the plurality of data samples indicate movement of a wearer wearing the article;

correlating the plurality of data samples with one or more of the first plurality of measurements of light and the second plurality of measurements of light; and removing, from one or more of the first plurality of measurements of light and the second plurality of measurements of light, a contribution of the movement.

14. A non-transitory computer-readable storage medium storing computer-executable program instructions, wherein when executed by a processing device, the computer-executable program instructions cause the processing device to perform operations comprising:

obtaining a first plurality of normalized measurements of light, wherein obtaining the first plurality of measurements of light comprises, for each measurement:

causing a first light source to transmit a pulse of light through an article to an area of skin, wherein the first light source is positioned in a first configuration;

determining a first measurement of light returned from the article;

responsive to determining that an energy level of the first plurality of measurements of light is lower than a threshold obtaining, a second plurality of measurements of light, wherein obtaining the second plurality of measurements of light comprises, for each measurement:

causing a second light source to transmit a second pulse of light through the article to the area of skin, wherein the second light source is positioned in a second configuration that is different from the first configuration; and obtaining a second measurement of light returned from the article;

determining, from the first plurality of measurements of light and the second plurality of measurements of light, a periodic change in an amplitude; and identifying the periodic change in amplitude as a heart rate based on the periodic change in amplitude.

15. The non-transitory computer-readable storage medium of claim 14, wherein when executed by a processing device, the computer-executable program instructions cause the processing device to perform operations comprising:

removing an ambient light signal from one or more of the first plurality of measurement of light and the second plurality of measurement of light.

16. The non-transitory computer-readable storage medium of claim 14, wherein when executed by a processing device, the computer-executable program instructions cause the processing device to perform operations comprising:

obtaining, via an inertial measurement device, a plurality of data samples; and responsive to determining that the heart rate is below a heart rate threshold, determining, from the plurality of data samples, that an infant wearing the article is asleep in a moving carrier.

17. The non-transitory computer-readable storage medium of claim 14, wherein when executed by a processing device, the computer-executable program instructions cause the processing device to perform operations comprising:

determining a rate of change in one or more of (i) the periodic change in amplitude or (ii) an envelope modulation of the first plurality of measurements of light and the second plurality of measurements of light; and identifying a respiratory rate as equal to the rate of change.

18. The non-transitory computer-readable storage medium of claim 14, wherein identifying the periodic change in amplitude comprises:

obtaining a plurality of frequency components by transforming one or more of the first plurality of measurements of light and the second plurality of measurements of light into a frequency domain; and identifying, from the plurality of frequency components, a component comprising a highest energy content.

19. The non-transitory computer-readable storage medium of claim 14, wherein identifying the periodic change in amplitude comprises:

obtaining, via an inertial measurement device, a plurality of data samples;

determining that the plurality of data samples indicate movement of a wearer wearing the article;

correlating the plurality of data samples with one or more of the first plurality of measurements of light and the second plurality of measurements of light; and removing, from one or more of the first plurality of measurements of light and the second plurality of measurements of light, a contribution of the movement.

20. The non-transitory computer-readable storage medium of claim 14, wherein when executed by a processing device, the computer-executable program instructions cause the processing device to perform operations comprising:

adjusting one or more of the first plurality of measurements of light and the second plurality of measurements of light to compensate for a contribution of the article based on one or more known properties of the article.

* * * * *